(12) United States Patent
Jetter et al.

(10) Patent No.: US 8,858,072 B2
(45) Date of Patent: Oct. 14, 2014

(54) MULTIPLE TEMPERATURE MEASUREMENTS COUPLED WITH MODELING

(71) Applicant: LifeScan, Inc., Milpitas, CA (US)

(72) Inventors: Thomas Jetter, Mainz (DE); Klaus Neubert, Esthal (DE); Thomas M. Weber, Darmstadt (DE); Mahyar Z. Kermani, Pleasanton, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 13/652,629

(22) Filed: Oct. 16, 2012

(65) Prior Publication Data
US 2013/0039383 A1 Feb. 14, 2013

Related U.S. Application Data

(62) Division of application No. 12/603,137, filed on Oct. 21, 2009, now Pat. No. 8,313,237.

(60) Provisional application No. 61/106,994, filed on Oct. 21, 2008.

(51) Int. Cl.
| | | |
|---|---|---|
| G01K 3/00 | (2006.01) | |
| G01K 13/00 | (2006.01) | |
| G01K 1/00 | (2006.01) | |
| G01K 7/00 | (2006.01) | |

(52) U.S. Cl.
USPC ............ 374/110; 374/141; 374/166; 374/208

(58) Field of Classification Search
USPC ................... 374/110, 141, 166, 208
See application file for complete search history.

(56) References Cited

U.S. PATENT DOCUMENTS

| | | |
|---|---|---|
| 5,077,476 A | 12/1991 | Rosenthal |
| 5,405,511 A | 4/1995 | White et al. |
| 5,497,772 A | 3/1996 | Schulman et al. |
| 6,880,968 B1 | 4/2005 | Haar |
| 7,407,811 B2 | 8/2008 | Burke et al. |
| 2005/0281312 A1 | 12/2005 | Chana |
| 2006/0229502 A1 | 10/2006 | Pollock et al. |
| 2009/0098657 A1 | 4/2009 | Blais et al. |
| 2010/0128754 A1 | 5/2010 | Jetter et al. |
| 2010/0319436 A1* | 12/2010 | Sun et al. ..................... 73/61.46 |
| 2012/0076171 A1* | 3/2012 | Wu ............................... 374/183 |

* cited by examiner

*Primary Examiner* — Mirellys Jagan
(74) *Attorney, Agent, or Firm* — Baker & Hostetler LLP

(57) ABSTRACT

The present invention is directed to, inter alia, systems and methods for calculating a temperature associated with an analyte measurement component of a biosensing instrument (such as a blood glucose monitor), with a test strip that is inserted in a biosensing instrument, or both. The present systems and methods may employ at least two temperature sensors, and the acquired temperature information may be used to modulate data regarding an analyte in a biological sample, thereby providing a more accurate measurement of the analyte.

25 Claims, 5 Drawing Sheets

MULTIPLE TEMPERATURE MEASUREMENTS COUPLED WITH MODELING

CROSS REFERENCE TO RELATED APPLICATION

The present application is a divisional of U.S. Ser. No. 12/603,137, filed Oct. 21, 2009, which claims priority to U.S. Provisional App. No. 61/106,994, filed Oct. 21, 2008, both of which are hereby incorporated by reference in their entireties.

TECHNICAL FIELD

The present invention relates to the detection of analyte levels by medical diagnostic systems such as blood glucose meters.

BACKGROUND

Biosensing instruments are used for the detection of various analytes (e.g., glucose and cholesterol) in blood samples. For example, blood glucose meters are medical diagnostic instruments used to measure the level of glucose in a patient's blood, and may employ disposable sample strips having a well or reaction zone for receiving a blood sample. Some meters include sensor assemblies that determine glucose levels by measuring the amount of electricity that can pass through a sample of blood, while other meters include sensor assemblies that measure how much light reflects from a sample. A computer microprocessor of the meter then uses the measured electricity or light from the sensor assembly to compute the glucose level and displays the glucose level as a number.

An important limitation of electrochemical methods of measuring the concentration of a chemical in blood is the effect of confounding variables on the diffusion of analyte and the various active ingredients of the reagent. For example, analyte readings are influenced by the ambient temperature that surrounds the sample well or reaction zone. As with any electrochemical sensing method, transient changes in temperature during or between measurement cycles can alter background signal, reaction constants and/or diffusion coefficients. Accordingly, a temperature sensor may be used to monitor changes in temperature over time. A maximum temperature change over time threshold value can be used in a data screen to invalidate a measurement. Absolute temperature threshold criteria can also be employed, wherein detection of high and/or low temperature extremes can be used in a data screen to invalidate a measurement. The microprocessor of a glucose sensor can make a determination as to whether the temperature of the testing environment is within predetermined thresholds, and prohibit a user from running a test if accuracy would be negatively affected. It is important, therefore, that any temperature sensing elements of the glucose meter not be affected by heat generated within the glucose meter (e.g., by a backlight liquid crystal display).

The temperature sensing elements of the glucose meter should have access to the ambient temperature surrounding the meter. In view of the temperature sensitivity of the biochemical reactions that are interpreted by a biosensing device, ambient temperature values that are obtained by temperature sensors are directly used during the assessment of analyte levels in the sample. As a consequence, even relatively minor variations in sensed ambient temperatures can create fluctuations in biochemical readings and result in erroneous outputs. Because the outputs provided by the biosensing device is intended to influence the patient's decisions regarding, inter alia, dosing of medication, it is very important that erroneous readings be avoided. Thus, biosensing instruments should include means for avoiding erroneous outputs that result from inaccurate or misleading ambient temperature readings.

Various prior art instruments employ internal or external thermal sensors in order to acquire information about the ambient temperature (see e.g., U.S. Pat. No. 5,405,511; U.S. Pub. No. 2006/0229502), while other instruments attempt to control the temperature of the reaction zone, and still other devices attempt to obtain indirect measurements of blood sample temperature by use of complex algorithms that rely upon the use of an ambient temperature sensor in combination with AC admittance measurements (see U.S. Pat. No. 7,407,811).

While sensors that are sensitive to ambient temperature are capable of rapidly reacting to a temperature change and thereby provide timely information, under certain circumstances this attribute can have undesired consequences. For example, when a biosensing instrument that is normally held in a user's hand is placed on a tabletop, a rapid temperature change may occur that can bias subsequent biochemical readings until ambient temperature readings have stabilized. As for instruments that attempt to control the temperature of the reaction zone, if the biosensing instrument is battery-driven, it becomes impractical to control the reaction zone temperature as this requires too great a power drain from the instrument's battery. Furthermore, certain approaches, such as that described in U.S. Pat. No. 7,407,811 do not provide a universal solution to the problem of estimating ambient temperature; the approach described in that patent is designed for use with a specific glucose strip, and if the strip chemistry or strip geometry changes, the disclosed algorithm must be modified. There remains a need for temperature sensing systems that can overcome these problems and otherwise improve the accuracy of analyte measurements by biosensing instruments.

SUMMARY

In one aspect of the present invention, provided are systems comprising a housing that substantially defines an internal space; an analyte measurement component that is within the housing or proximate the housing; a first temperature sensor that is disposed at a first position within the housing and is in thermal communication with a heat source; a second temperature sensor that is disposed at a second position within the housing and is in thermal communication with the heat source to a lesser extent relative to the first temperature sensor; and, a processor that is disposed within the housing, is in electronic communication with the first temperature sensor and the second temperature sensor, and uses temperature data from the temperature sensors to calculate a temperature associated with the analyte measurement component.

Also disclosed are systems comprising a housing that substantially defines an internal space; an analyte measurement component that is within the housing or proximate the housing; a first temperature sensor that is disposed at a first position within the housing and is in thermal communication with a heat source; a second temperature sensor that is disposed at a second position within the housing and is in thermal communication with the ambient environment outside of said housing to a greater extent relative to said first temperature sensor; and, a processor that is disposed within the housing, is in electronic communication with the first temperature sensor and the second temperature sensor, and uses temperature data from the temperature sensors to calculate a temperature associated with the analyte measurement component.

In yet another aspect, provided are methods for calculating a temperature associated with a test strip inserted in an analyte assessing system comprising measuring a first temperature at a first position that is in thermal communication with a heat source in the analyte assessing system; measuring a second temperature at a second position in the analyte assessing system that is in thermal communication with the heat source to a lesser extent relative to the first position; and, using the measured first temperature and the measured second temperature to calculate the temperature associated with the test strip.

DETAILED DESCRIPTION OF ILLUSTRATIVE EMBODIMENTS

Figure 1A:
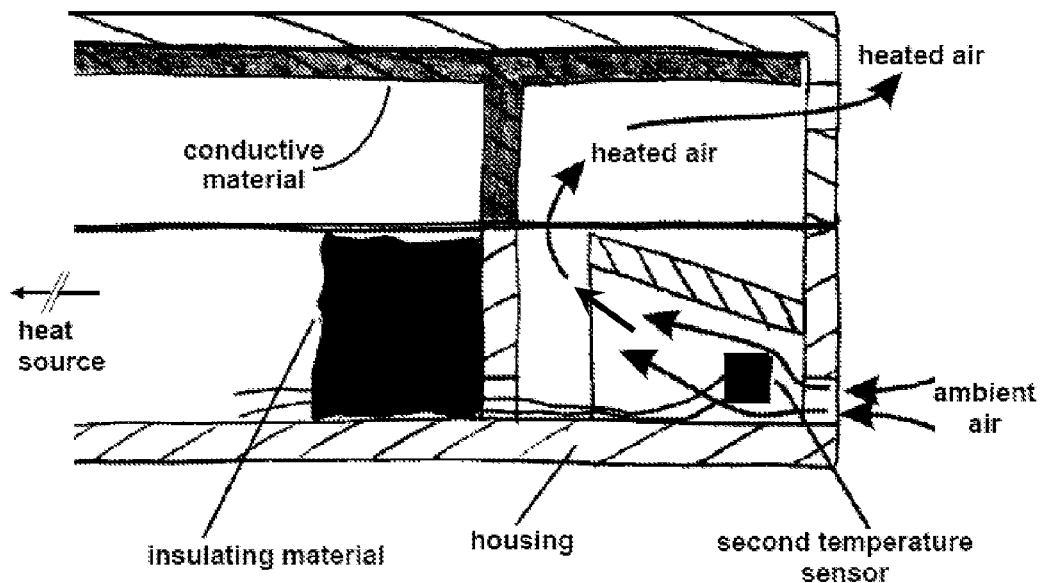
FIGS. 1A and 1B respectively depict embodiments of the present invention that permit the displacement of heated air proximate the second temperature sensor.

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The use of one or more temperature sensors, for example, thermistors, thermometers, or thermocouple devices, to measure the ambient temperature surrounding a biosensing instrument can provide information that may be used to improve the accuracy of measurement of one or more analytes in a biological sample. However, such methods fail to consider, and indeed may deliberately discount, the effect on the determination of ambient temperature by heat that is generated from one or more components of the biosensing instrument. It has presently been discovered that the acquisition of temperature measurements at a position within a biosensing instrument that is in thermal communication with a heat source, in addition to the measurement of temperature that approximates the ambient environment outside of the instrument, can improve an instrument's ability to conduct accurate measurements of an analyte in the test sample by allowing the instrument to compensate for the actual temperature conditions affecting the reaction of the sample with the strip's sensor assembly. The presently disclosed process of "dual temperature" measurement improves the ability of the biosensing instrument to provide accurate readings regarding analyte levels, which has a positive effect on a user's ability to obtain the medical information required to make appropriate and timely decisions regarding medication, consultation with a doctor or nurse, or other treatment options. Furthermore, the present invention permits a temperature determination that is independent of the device orientation, power fluctuation, and other factors that can skew temperature readings in devices in which sensors are only used to estimate ambient temperature, rather than measure both ambient temperature and temperature at a position within a biosensing instrument that is in thermal communication with a heat source.

In one aspect of the present invention, provided are systems comprising a housing that substantially defines an internal space; an analyte measurement component that is within the housing or proximate the housing; a first temperature sensor that is disposed at a first position within the housing and is in thermal communication with a heat source; a second temperature sensor that is disposed at a second position within the housing and is in thermal communication with the heat source to a lesser extent relative to the first temperature sensor; and, a processor that is disposed within the housing, is in electronic communication with the first temperature sensor and the second temperature sensor, and uses temperature data from the temperature sensors to calculate a temperature associated with the analyte measurement component.

Also disclosed are systems comprising a housing that substantially defines an internal space; an analyte measurement component that is within the housing or proximate the housing; a first temperature sensor that is disposed at a first position within the housing and is in thermal communication with a heat source; a second temperature sensor that is disposed at a second position within the housing and is in thermal communication with the ambient environment outside of said housing to a greater extent relative to said first temperature sensor; and, a processor that is disposed within the housing, is in electronic communication with the first temperature sensor and the second temperature sensor, and uses temperature data from the temperature sensors to calculate a temperature associated with the analyte measurement component.

In yet another aspect, provided are methods for calculating a temperature associated with a test strip inserted in an analyte assessing system comprising measuring a first temperature at a first position that is in thermal communication with a heat source in the analyte assessing system; measuring a second temperature at a second position in the analyte assessing system that is in thermal communication with the heat source to a lesser extent relative to the first position; and, using the measured first temperature and the measured second temperature to calculate the temperature associated with the test strip.

Unless otherwise specified, the description of a particular embodiment, feature, component, or functionality applies both to present methods and the present systems. For example, reference to a "system" applies both to the "analyte assessing systems" of the present methods and to the "systems" as separately claimed.

The present systems include a housing that substantially defines an internal space. The housing may be made from any suitable material and may adopt any appropriate configuration that can accommodate those components of the system that must be internal to the housing. Many biosensing instruments have housings that comprise a plastic shell assembled from one or more molded parts. For example, the housing may be a shell comprising a first and a second half, one half forming the "upper" portion of a device in a horizontal resting position (such as on a tabletop, such that the long axis of the device is substantially parallel to the surface of the tabletop—if the device does not have a long axis, then a "horizontal" orientation may refer to the resting position of the device when in use, e.g., whereby the interactive components such as the display, buttons, and the like, are facing upwards on the opposite face of the device that is in contact with the surface, or may refer to the condition whereby the axis formed by an imaginary line between the second temperature sensor and a heat source is substantially parallel to the surface), and the other half forming the "lower" portion of the device, the two halves having been configured to allow their secure attachment to one another in order to form an integrated shell, and to accommodate internal components, components that may be partially external to the housing (such as switches, interface buttons, display components, etc.), features necessary for the assembly of the housing (such as interlocking parts, or screw or rivet holes), batteries (i.e., the housing may include a battery port and/or battery door), air vents, and the like. The housing may also feature one or more coated sections that enhance the user's ability to grip the biosensing instrument, such as rubber gripping portions on the outer lateral sides of the housing. Those skilled in the art will readily appreciate the size, shape, and material parameters that may suitably be used to form a housing of an analyte measurement system.

The analyte measurement component is disposed within the housing or proximate the housing. In other words, the analyte measurement component may be partially or completely disposed within the housing, may be mounted or otherwise affixed to the housing, may be at least partially defined by the housing, or may be any combination thereof. The analyte measurement component may include an aperture for receiving a test strip and can measure an analyte on the test strip, i.e., can measure an analyte that is present within a biological sample on the test strip, thereby providing analyte measurement data, which can be communicated to another component of the system. Analyte measurement components are found in traditional biosensing instruments, for example, whereby the aperture is located at one end of the housing (which may in fact be molded such as to define the aperture) and includes electrical components that contact the inserted end of a test strip and receive the electrical signals that have traveled to the inserted end of the test strip from the end of the strip that holds the biological sample. The aperture typically includes a groove or slot having the same width as a test strip, into which the test strip is inserted by the user. The electrical components interface with processing equipment inside the housing, such as a microprocessor, to which the electrical components supply analyte measurement data corresponding to the signals received from the test strip. Various configurations for the analyte measurement component will be readily appreciated by those having ordinary skill in the art, who will recognize that the analyte measurement component of the present invention may be configured in a manner that is similar to analyte measurement components of traditional biosensing instruments.

Each of the first and second temperature sensors may be any device capable of detecting static and/or dynamic temperature conditions. Those skilled in the art will readily appreciate that any of various types of temperature sensors may be used, including, inter alia, thermistors, thermometers, or thermocouple devices. The first temperature sensor is disposed at a first position within said housing and is in thermal communication with a heat source. Modern biosensing instruments are typically compact devices, and often incorporate liquid crystal displays with backlight, processors for data processing, radio-frequency components for wireless communication, and many other electronic components or subassemblies; such components consume power and they result in heat dissipation. The interior temperatures of compact devices with internal power dissipation can rise, sometimes significantly, above the ambient temperature, which can mean that a measurement of temperature using a single internal thermistor may not be representative of the actual ambient temperature. This can in turn influence analyte readings derived from a sample well or reaction zone of a test strip. In accordance with the present invention, the first temperature sensor is in thermal communication with a "heat source" (i.e., at least one heat-generating component or subassembly that is included as part of a biosensing instrument) and can be used to account for the effect of the heat generated by the heat source on the determination of a temperature associated with the analyte measurement component. Information regarding the use of temperature data from the first and second temperature sensors in calculating a temperature associated with the analyte measurement component is described infra. As used herein, "thermal communication" between two components or between a component and an environment preferably refers to the exposure of a component to heat conditions associated with the other component or with the environment; varying degrees of thermal communication may exist between components or between a component and a particular environment, such that with respect to a first component that emits heat or an environment possessing certain temperature conditions, a second component may be in thermal communication with the first component or the environment to a lesser or greater extent than a third component.

Unless otherwise specified, the first temperature sensor may comprise more than one discrete temperature sensing device. Thus, more than one temperature sensor in thermal communication with a heat source may be present. Where multiple "first" temperature sensors are present, each may be in thermal communication with the same heat source, each may respectively be in thermal communication with a different heat source, or some may be in thermal communication with one heat source while one or more are in thermal communication with a different heat source. Accordingly, where multiple "first" temperature sensors are present, one or more of the sensors may be disposed at or near the same position within the housing, or each of the respective "first" temperature sensors may be disposed at different positions within the housing (preferably each of the positions at which the "first" temperature sensors are disposed are different from the location of any second temperature sensor).

Insulating material may be interposed between a first temperature sensor and a heat source. Insulating material comprises any substance or condition that increases heat transfer resistance between the first temperature sensor and the heat source. For example, the insulating material may be rubber, plastic, metal, a foam (such as polyurethane foam, styrofoam, and the like), or any other suitable material, many types of which are readily appreciated by those skilled in the art. Where multiple "first" temperature sensors are present, insulating material may be disposed between some or all of the "first" temperature sensors and the heat source that is physically closest to a given "first" temperature sensor.

The second temperature sensor is disposed at a second position with the housing and is in thermal communication with the heat source to a lesser extent relative to the first temperature sensor. For example, the second temperature sensor may be in thermal communication with the heat source to a lesser extent by virtue of spatial displacement (i.e., the distance between the second temperature sensor and the heat source is greater than the distance between the first temperature sensor and the heat source), the existence of one or more physical barriers to heat between the second temperature and the heat source (or the existence of greater numbers of or more highly efficacious thermal barriers between the second temperature and the heat source as compared with the number or efficacy of the thermal barrier(s) between the first temperature sensor and the heat source), or any combination thereof. When "the heat source" comprises more than one heat-generating component or subassembly that is included as part of a biosensing instrument, the second temperature sensor is in thermal communication with the combined amount of heat emitted from the more than one heat generating component or subassembly to a lesser extent relative to the exposure of the first temperature sensor to the combined amount of heat emitted from the more than one heat generating component or subassembly.

In other embodiments of the present invention, the second temperature sensor is disposed at a second position with the housing and is in thermal communication with the ambient environment outside of the system housing to a greater extent relative to the first temperature sensor. In such instances, there may be fewer physical thermal barriers, thermal barriers that are less efficacious, or less spatial displacement between the second temperature and the ambient environment, or there may be more thermal barriers, more efficacious thermal barriers, more spatial displacement between the first temperature sensor and the ambient environment as compared with the second temperature sensor, or any combination thereof.

Unless otherwise specified, the second temperature sensor may comprise more than one discrete temperature sensing device. Thus, more than one temperature sensor that is in thermal communication with the heat source to a lesser extent relative to the first temperature sensor may be present. Where multiple "first" and "second" temperature sensors are present, with respect to a given "second" temperature sensor, such sensor should be in thermal communication with a heat source to a lesser extent relative to at least one "first" temperature sensor, or should be in thermal communication with the ambient environment outside of the system housing to a greater extent relative to at least one "first" temperature sensor.

Insulating material may be interposed between a second temperature sensor and a heat source. Insulating material comprises any substance or condition that increases heat transfer resistance between the second temperature sensor and the heat source. For example, the insulating material may be rubber, plastic, metal, a foam (such as polyurethane foam, styrofoam, and the like), or any other suitable material, many types of which are readily appreciated by those skilled in the art. Such insulating material may be present at the same time that insulating material is interposed between a first temperature sensor and a heat source. Where multiple "second" temperature sensors are present, insulating material may be disposed between some or all of the "second" temperature sensors and the heat source that is physically closest to a given "second" temperature sensor.

In other embodiments, insulating material may be interposed between a first temperature sensor and a second temperature sensor. As provided above, insulating material comprises any substance or condition that can serve to increase heat transfer resistance—here, as between a first temperature sensor and a second temperature sensor. Such insulating material may be present at the same time that (i.e., in the same embodiment in which) insulating material is interposed between a first temperature sensor and a heat source, between a second temperature sensor and a first temperature sensor, or both. Where multiple "first" and/or "second" temperature sensors are present, insulating material may be disposed between only one of the "first" and one of the "second" temperature sensors, or between some or all of the "first" temperature sensors and "second" temperature sensors.

Any combination of insulating material interposed between a first temperature sensor and a heat source, insulating material interposed between a second temperature sensor and a heat source, and insulating material interposed between a first temperature sensor and a second temperature sensor may be used in accordance with the present invention.

The temperature readings respectively performed by the first and second temperature sensors may occur simultaneously, or may take place at different times relative to one another. Spatial and optionally temporal variation between or among the first temperature sensor(s) and second temperature sensor(s) may be used to enhance the accuracy of the calculation of a temperature associated with the analyte measurement component, a test strip, or both.

The first and second temperature sensors are in electronic communication with a processor that is disposed within the housing and that uses temperature data from the temperature sensors to calculate a temperature associated with the analyte measurement component. Electronic communication refers to direct or indirect electronic communication, such that the processor may receive temperature data directly from one or both of the first and second temperature sensors, or the processor may receive temperature data from a component that accepts data from one or both of the first and second temperature sensors and transfers such data to the processor. The processor may also receive analyte measurement data directly or indirectly from the analyte measurement component, and may use the temperature data from the temperature sensors to modulate the analyte measurement data. The processor that modulates the analyte measurement data using the temperature data may be a central processing unit that receives the temperature data and the analyte measurement data, respectively, from other processor components.

The second temperature sensor ideally provides temperature data that substantially corresponds to the temperature of the ambient environment outside of the housing. To this end, the systems of the present invention may preferably adopt any configuration that permits exposure of the second temperature sensor to temperature conditions that approximate those of the ambient environment, even as, for practical purposes (such as to prevent damage to the sensor), the second temperature sensor is disposed within the housing.

In some embodiments, ambient air (that is, air from the ambient environment outside of the housing, or air having the same temperature as the ambient environment outside of the housing) contacts the second temperature sensor and displaces heated air proximate the second temperature sensor. For example, the present systems may comprise a first opening in the housing at a location proximate the second temperature sensor, a second opening at a second location in the housing, a channel extending between the first opening and the second opening and containing the second temperature sensor, wherein each of the openings place the channel in fluid communication with the ambient environment outside of the housing. "Fluid communication" between two locations refers to the ability of air to flow therebetween. Likewise, the present systems may comprise a convection system that permits air flow from the ambient environment outside of the housing into at least a portion of the internal space, wherein the air flow displaces heated air proximate the second temperature sensor. As used herein, "heated air" refers to air having a temperature that is elevated beyond that of the ambient environment outside of the housing of the biosensing instrument, wherein the elevation in temperature is typically attributable to heat-dissipation by one or more components of the biosensing instrument. A convection system can result from the creation of a temperature differential between two locations within the housing. For example, the heat dissipated within the housing will typically be transferred to an upper portion of the housing and the lower portion of the housing may be isolated from the heat source using appropriate insulating material. The temperature difference between the lower portion of the housing and the upper portion of the housing creates airflow.

FIG. 1A depicts a side view embodiment of the present invention (the near side wall of the housing is omitted in order to allow viewing of components inside of the housing) whereby ambient air enters the housing via an opening, flows over the second temperature sensor, and displaces heated air proximate the second temperature sensor so that the heated air flows out of a second opening in the housing. The path of the air flow (arrows) corresponds to the contours of a channel that is preferably oriented substantially vertically within a biosensing instrument when that instrument is placed in a horizontal, resting position on a flat surface. In FIG. 1A, insulating material, such as that described supra, is used to increase heat transfer resistance between the second temperature sensor and one or more heat sources located in other portions of the housing (not shown), and conducting material, such as metal, is used to provide better heat conductivity than the portion of the housing proximate the second temperature sensor to create a temperature differential within the housing and thereby further encourage heat flow away from the second temperature sensor.

Figure 1B:
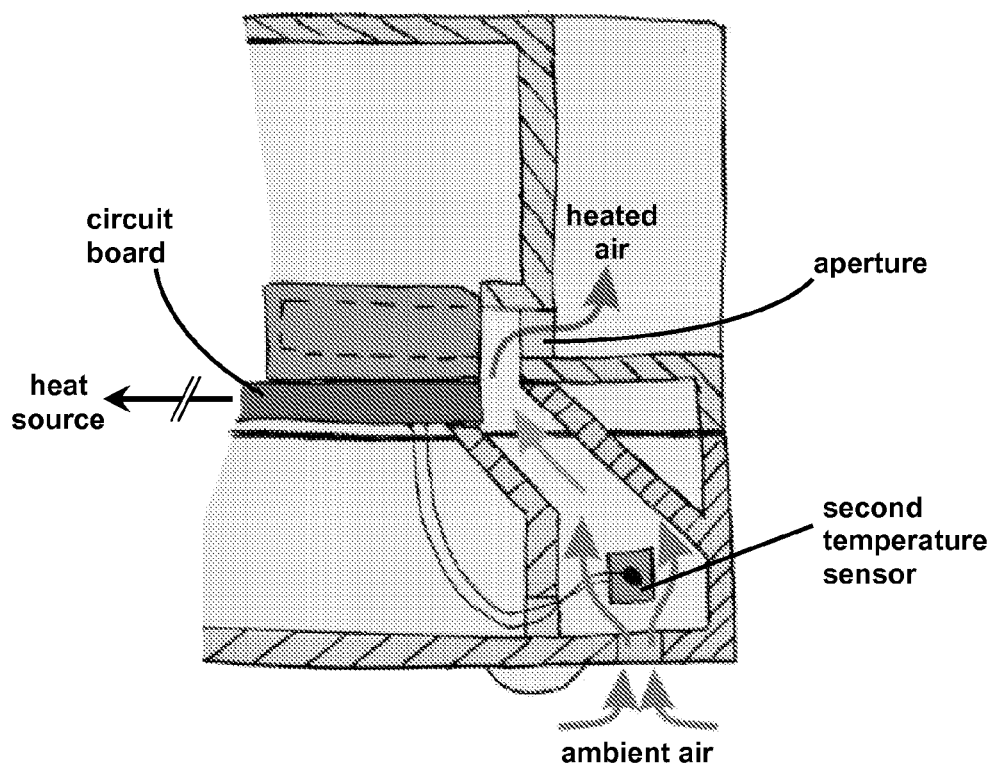

In other embodiments, one or more heat sources generate heat for forming the heated air that is displaced by ambient air. Thus, one or more heat sources may generate heated air in order to allow the formation of a convection system that permits air flow from the ambient environment outside of the housing and the consequent displacement of heated air proximate the second temperature sensor. In some embodiments, heated air is formed by heat transferred from a heat source via a transfer element that contacts the heat source. For example, heat that is transferred from a heat source (such as a microprocessor) via a circuit board can form the heated air. As provided above, heat sources associated with a biosensing instrument may include liquid crystal displays with backlight, processors for data processing, radio-frequency components for wireless communication, and many other power-consuming electronic components or subassemblies. In some embodiments, the channel through which ambient air from the environment outside of the housing may be in at least partial thermal communication with a heat source. FIG. 1B depicts an embodiment wherein the channel is in thermal communication with a heat source (e.g., a microprocessor—not shown) via a printed circuit board (PCB) on which the heat source is mounted; the PCB is not separated from the channel by insulating material, and in fact generates heated air that is displaced by air flowing from the ambient environment outside of the housing. The path of the air flow (arrows) corresponds to the contours of a channel that is preferably oriented substantially vertically within a biosensing instrument when that instrument is placed in a resting position on a flat surface. An arrangement of the variety depicted in FIG. 1B may obviate the need to use conductive material (e.g., as in FIG. 1A). In addition, in accordance with such embodiments, the aperture into which the strip is inserted may function as the "second opening" through which heated air that is displaced from the second temperature sensor exits the channel, thereby obviating the need to provide a separate "second opening".

The present systems may adopt any other configuration that permits the exposure of the second temperature sensor to temperature conditions that approximate those of the ambient environment. In certain embodiments, the present systems may be configured to reduce the heat transfer resistance between the second temperature sensor and the ambient environment outside of said housing. In other embodiments, the present systems may be configured to increase the effective contact surface area between the second temperature sensor and the ambient environment outside of the housing. For example, the second temperature sensor may be positioned proximate an opening in the housing. The "contact" between the second temperature sensor and the ambient environment need not be direct, and may be mediated by a component having low heat resistance. For example, the second temperature sensor may be positioned proximate an opening in the housing, and heat conductive material may be disposed between the second temperature sensor and the opening in the housing. "Heat conductive material" may refer to any material that provides a lower heat transfer resistance than the material from which the housing is substantially formed; for example, the heat conductive material may be metal (such as aluminum, copper, steel, silver, or a metal alloy like brass, and the like), plastic, glass, or any other suitable material. Alternatively, the heat conductive material may be the same material as that from which the housing is substantially formed, but having a thinner cross-section so that heat transfer resistance across the heat conductive material is decreased relative to the heat transfer resistance across a portion of the housing. The second temperature sensor may be mounted on the heat conductive material that is disposed between the sensor and the opening in the housing. In some embodiments, a "heat sink" material may be disposed between the heat conductive material and the sensor. The heat sink material may be any substance having low heat transfer resistance such as to minimize the heat transfer path between the ambient environment outside of the housing and the second temperature sensor. Heat sink materials may be fluid or paste-like substances that increase the thermal conductivity of a thermal interface, for example, by compensating for the irregular surfaces of the components that are linked by the heat sink material. Examples include thermal grease, thermal paste, and other materials that will be readily appreciated by those skilled in the art.

Figure 2:
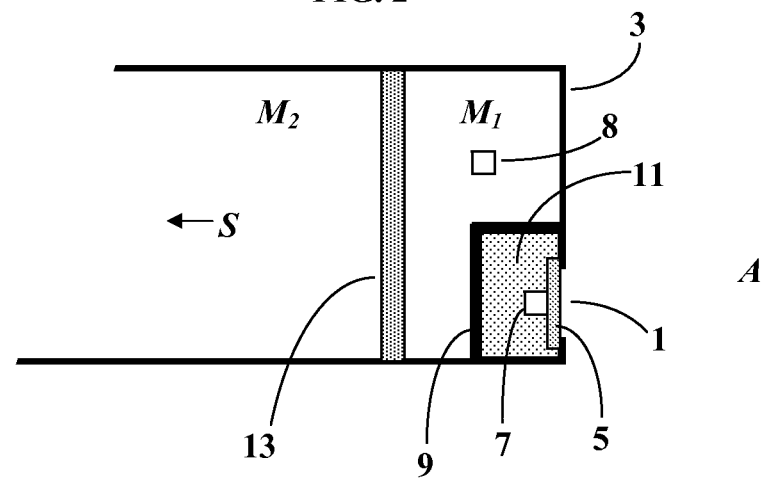
FIG. 2 depicts an embodiment of the present invention in which the second temperature sensor is positioned proximate an opening in the housing in order to decrease heat transfer resistance between the second temperature sensor and the ambient environment outside of the housing.

The second temperature sensor, opening in the housing, and heat conductive material may be at least partially isolated from the remainder of the internal space defined by the housing. The isolation of the second temperature sensor, opening in the housing, and heat conductive material may comprise thermal isolation be accomplished through the use of insulating material as defined above (i.e., any material that increases heat transfer resistance). FIG. 2 depicts a horizontally-oriented side view of an embodiment of the present invention as it would appear if the system were placed in a resting position on a flat surface (i.e., such that the long axis of the system is substantially parallel to the flat surface; if the system did not have a long axis, "horizontal" orientation may refer to the condition whereby the axis formed by an imaginary line between the second temperature sensor and a heat source is substantially parallel to the surface); the near side wall of housing 3 is omitted in order to allow viewing of internal components. This embodiment includes an opening 1 in housing 3, over which a plate 5 of heat conductive material is disposed. Second temperature sensor 7 is mounted on plate 5, and these components are enclosed within insulating material 9, 11 in order to at least partially thermally isolate them from other portions of the internal space $M_1$, $M_2$. Plate 5 increases the effective contact surface area between the ambient environment A outside of the housing 3 and the second temperature sensor 7, which in turn lowers the heat transfer resistance between the ambient environment A and second temperature sensor 7.

If the orientation of the system is changed, for example, if the system were oriented vertically with second temperature sensor 7 at the "top" (rather than at the "side", as shown in FIG. 2), then it is possible that heat emitted from heat source S (actual component not shown) could reach second temperature sensor 7 by convection to a greater extent than when the system is oriented horizontally, and thereby introduce error into the temperature readings performed by the second temperature sensor 7. In order to minimize the effects of changes in orientation of the system, an optional heat convection barrier 13 comprising insulating material can be used to increase heat transfer resistance between $M_1$ (in which both the first temperature sensor 8 and the second temperature sensor 7 are located) and $M_2$ (in which heat source S is disposed). As demonstrated infra in Example 2, the inclusion of a heat convection barrier between a portion of the internal space of the system in which a heat source is located and the portion of the internal space of the system can correct for the effects of heat convection when the orientation of the system is changed, e.g., from horizontal to vertical, or vice versa.

The first and second temperature sensors are in electronic communication with a processor that is disposed within the housing and uses temperature data from the temperature sensors to calculate a temperature associated with the analyte measurement component. The system may then compensate for the calculated temperature associated with the analyte measurement component during a measurement of an analyte on a test strip. For example, the measurement of an analyte on a test strip may result in the acquisition of analyte measurement data that may be modulated in order to account for the temperature data acquired from the first and second temperature sensors. The calculation of a temperature associated with the analyte measurement component, the receipt of analyte measurement data, and any compensation for the calculated temperature associated with the analyte measurement component may be performed by separate processors that are in electronic communication with any of the first temperature sensor, second temperature sensor, and analyte measurement component, or each of these functions may be performed by a single multifunction processor. As used herein, "electronic communication" may be mediated by physical means (e.g., circuits), or may be "wireless". The processor that receives the analyte measurement data may be the same processor that receives temperature data from the first and second temperature sensors. Alternatively, the processor that modulates the analyte measurement data using the temperature data may be a central processing unit that receives the temperature data and the analyte measurement data, respectively, from other processor components. Various configurations for the processors and other components of the present systems will be readily appreciated among those skilled in the art, and any suitable configuration may be used in accordance with the present invention.

Figure 3A:
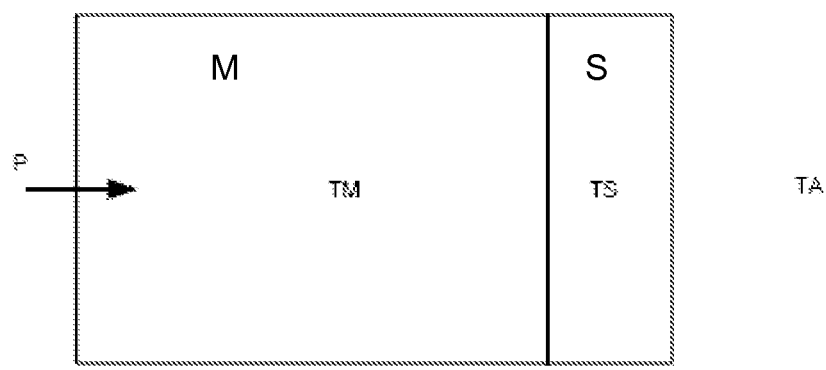
FIGS. 3A and 3B respectively illustrate a simplified thermodynamic model and a steady-state thermodynamic electrical equivalent circuit that may be used to describe certain aspects of the present invention.
Figure 3B:
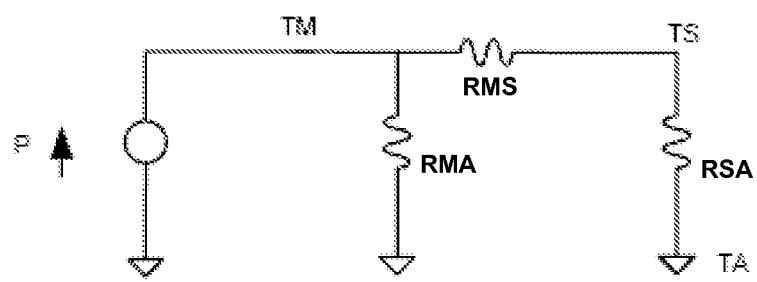

A simplified steady-state thermodynamic model may be used to describe the considerations undertaken pursuant to the present systems in order to calculate a temperature associated with the analyte measurement component and/or a test strip, and/or compensate for the calculated temperature associated with the analyte measurement component and/or a test strip during a measurement of an analyte. FIGS. 3A and 3B respectively provide a simplified thermodynamic model and a steady-state thermodynamic electrical equivalent circuit, in which the following abbreviations are employed:

| Symbol | Meaning |
| --- | --- |
| P | Power dissipation inside the device |
| M | Main area of the internal space within the housing where the main heat sources are located. |
| S | Area of the housing where the second temperature sensor S is positioned. The temperature values of S and M are the basis for the calculation of the temperature associated with the analyte measurement component |
| TM | Temperature measured by the first temperature sensor in the area M within the housing |
| TS | Temperature measured by the second temperature sensor in the area S within the housing |
| TA | Actual ambient temperature |
| RMA | Heat transfer resistance between the area M and the ambient environment outside of the housing |
| RMS | Heat transfer resistance between the area M and the second temperature sensor S |
| RSA | Heat transfer resistance between the second temperature sensor S and the ambient environment outside of the housing |

In a dynamic model there are heat capacitances for the housing and the temperature sensors that can be modeled as capacitors in the electrical equivalent model (FIG. 3B). In the steady state these capacitors are high impedance and can be ignored. Thus, the temperature difference (TS−TA) is calculated from the difference of (TM−TA) according to the relationship of RSA and RMS, so that the following formulas apply:

$$TS - TA = \frac{RSA}{RSA + RMS} \cdot (TM - TA) \quad \text{(For steady state)} \tag{1}$$

$$K = \frac{RSA}{RSA + RMS} \quad \text{(For steady state)} \tag{2}$$

$$K = \frac{(TS - TA)}{(TM - TA)} \quad \text{(For steady state)} \tag{3}$$

$$TA = TS + \frac{K}{K-1}(TM - TS) \quad \text{(For steady state)} \tag{4}$$

K is a constant that depends on the thermodynamic structure of the system as defined by equation (2). In practice, this constant is estimated by a series of temperature measurements of TM, TS and TA using equation (3). This constant is programmed into software used by the system. Then, using equation (4), the ambient temperature is estimated using TM, TS and K. As it is seen, the smaller the K, then TS is better representative of the ambient temperature.

In accordance with the present invention, a processor may calculate the temperature (TA) associated with the analyte measurement component by performing a calculation according to formula (I)

$$TA = TS + \frac{K}{K-1}(TM - TS) \quad \text{(I)}$$

wherein TS is the temperature measured by said second temperature sensor, TM is the temperature measured by the first temperature sensor, and K is defined by $$K = \frac{(TS - TA)}{(TM - TA)}$$

wherein TS is the temperature measured by the second temperature sensor, TA is the actual temperature of the ambient environment outside of said housing, and TM is the temperature measured by the first temperature sensor.

EXAMPLES

Example 1

Convection System

Figure 4A:
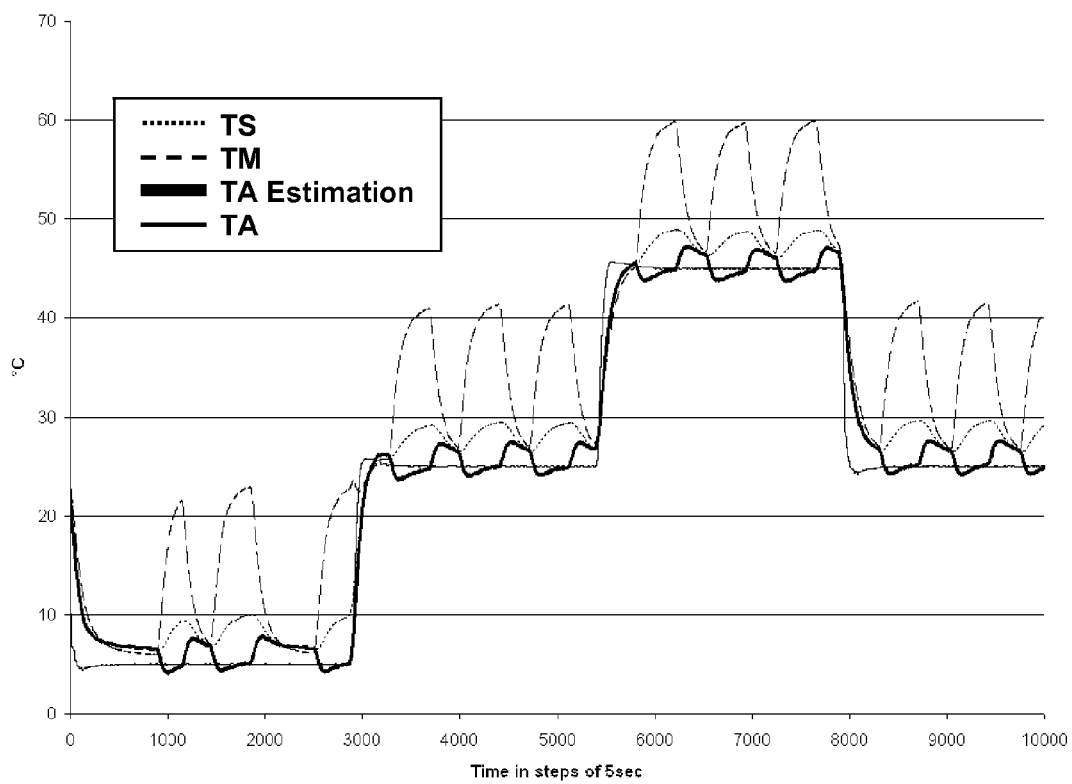
FIGS. 4A and 4B show the results of an evaluation of an embodiment of the present invention that was configured to provide a convection system that permits air flow from the ambient environment that displaces heated air proximate a second temperature sensor, and the temperature error associated with the test, respectively.
Figure 4B:
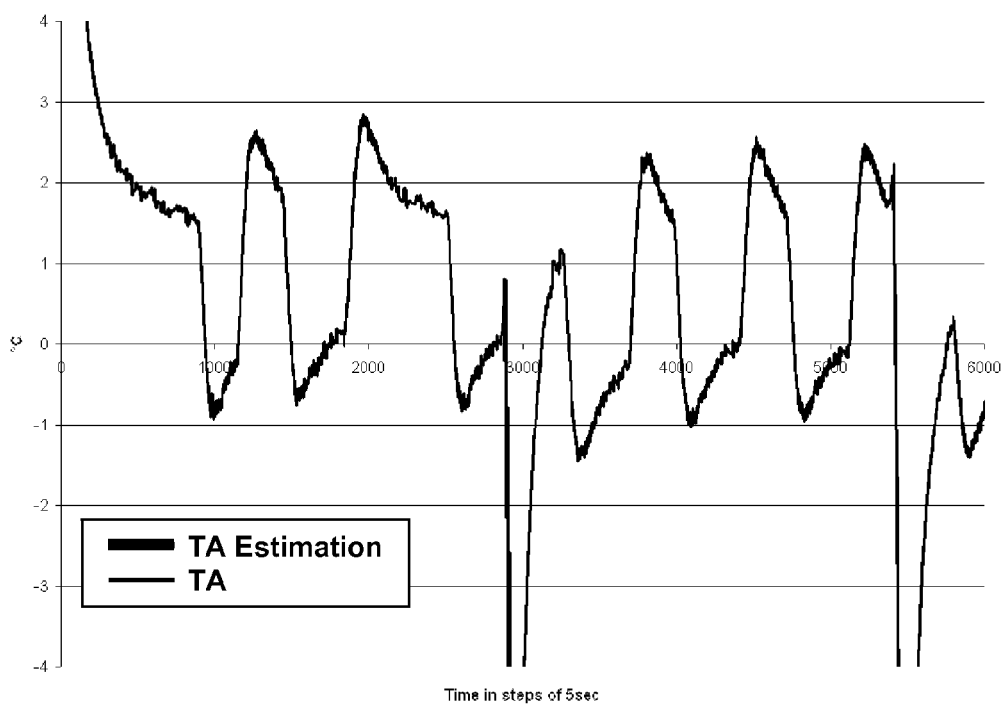

A climate chamber was used to test an exemplary system designed to provide a convection system for increasing the exposure of the second temperature sensor to air from the ambient environment. Foam rubber insulating material was used to form a chamber enclosing the second temperature sensor in order to increase heat transfer resistance between the second temperature sensor from the remainder of the internal space of the system defined by the housing. Openings in the housing were used to permit air flow from the ambient environment into the chamber and to permit the displacement of heated air proximate the second temperature sensor. The first temperature sensor was positioned on a circuit board, and the internal space inside of the housing was divided by insulating material into two main portions: M1, in which the first temperature sensor, circuit board, and the chamber containing the second temperature sensor were located, and M2, in which a heat source comprising a resistor having a power dissipation of approximately 1.4 W was located. The heat source was switched on and off during the experiment to simulate the behavior of the system during variable heat dissipation periods such as would occur during normal operation of a biosensing instrument. Temperature readings were acquired at 5 second intervals. FIG. 4A depicts results wherein TS represents the temperature readings acquired by the second temperature sensor, TM represents the temperature readings acquired by the first temperature sensor, TS Estimation represents the ambient temperature as calculated by the system using the first and second temperature sensor readings, and TA is the actual ambient temperature as separately measured within the test chamber. FIG. 4B shows the temperature error in the calculation of the temperature of the ambient environment outside of the housing (which is equivalent to a temperature associated with an analyte measurement component, a test strip, or both). Results are shown in 5 second intervals.

Example 2

System Increasing Effective Surface Contact Area with Ambient Environment

A climate chamber was used to test an exemplary system designed to increase the effective surface contact area between the second temperature sensor and the ambient environment. The experimental system included a housing having an opening over which a brass plate having a thickness of about 0.5 mm was placed. The second temperature sensor was mounted on the brass plate and the sensor/plate arrangement was enclosed within a chamber defined by insulating material. The insulating material defining the chamber was a layer of plastic housing material, i.e., a layer of the same type of plastic used to form the housing. A resistor with an external power supply that provided a power dissipation of about 1.4 W was placed within the interior space defined by the housing, outside of the chamber in which the sensor/plate arrangement was enclosed. The heat source was switched on and off during the experiment to simulate the behavior of the system during variable heat dissipation periods such as would occur during normal operation of a biosensing instrument. Temperature readings were acquired at 5 second intervals, the maximum period during which the resistor was operational was 0.5 hours.

Figure 5A:
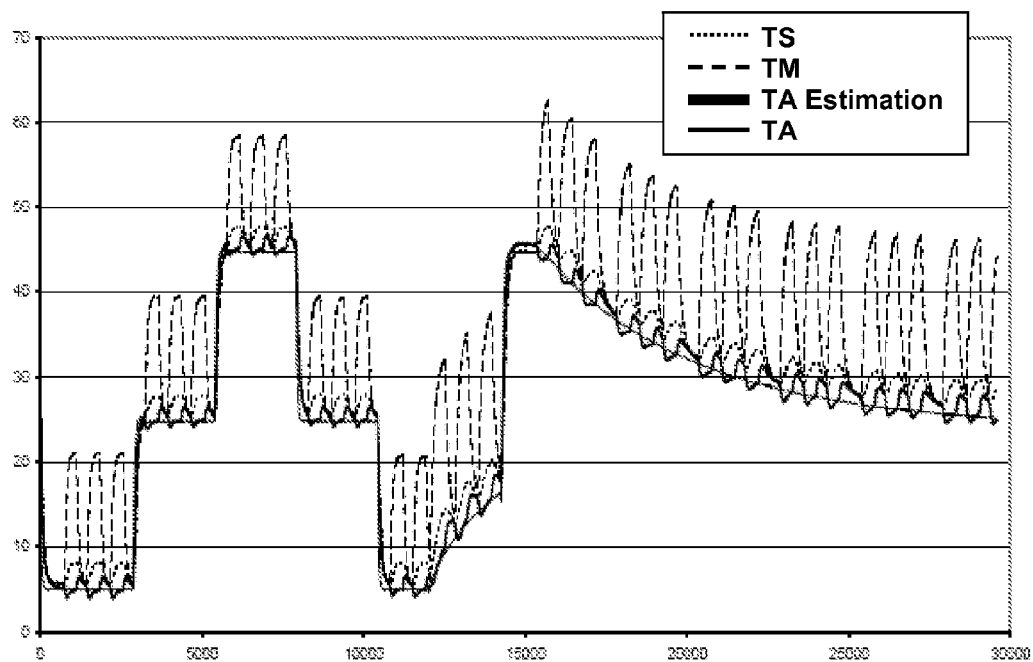
FIGS. 5A and 5B show the results of an evaluation of an embodiment of the present invention that was designed to increase the effective surface contact area between the second temperature sensor and the ambient environment, and the temperature error associated with the test, respectively.

FIG. 5A depicts results wherein TS represents the temperature readings acquired by the second temperature sensor, TM represents the temperature readings acquired by the first temperature sensor, TA Estimation represents the ambient temperature as calculated by the system using the first and second temperature sensor readings, and TA is the actual ambient temperature as separately measured within the test chamber.

Figure 5B:
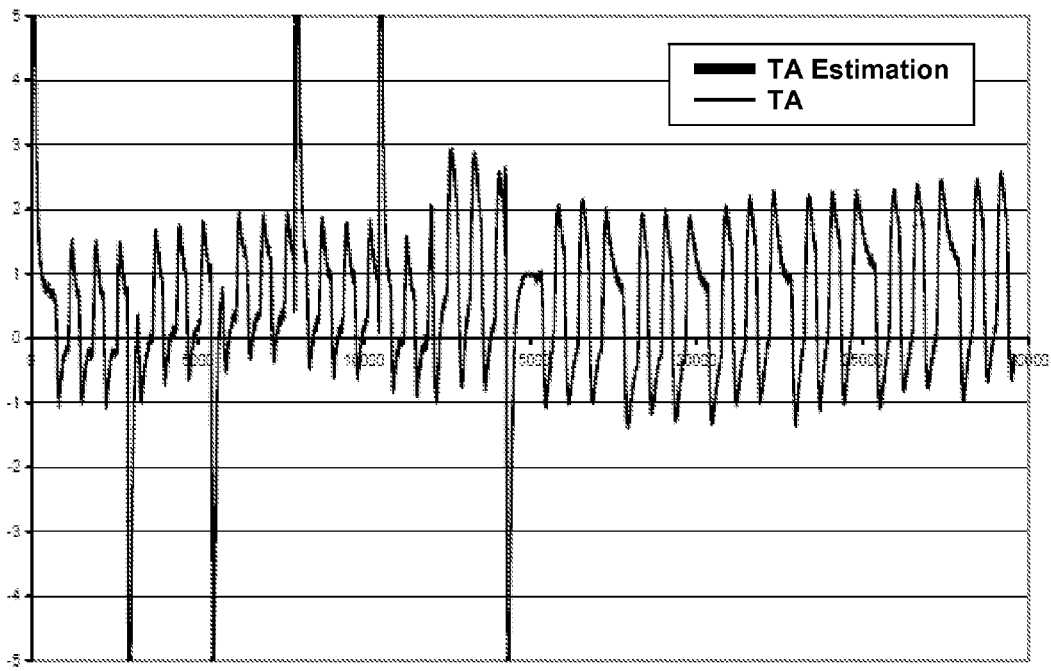

FIG. 5B shows the temperature error in the calculation of the temperature of the ambient environment outside of the housing (which is equivalent to a temperature associated with an analyte measurement component, a test strip, or both). Results are shown in 5 second intervals.

It was determined that the major sources of error with respect to the above-described system included sudden changes in ambient temperature, power dissipation fluctuations inside the system, and the orientation of the system relative to the ground. Large error spikes were observed when the ambient temperature changes rapidly; however, such rapid changes in ambient temperature are not typically encountered during ordinary use of a biosensing instrument. Thus, the areas of interest with respect to temperature error are fluctuations in heat dissipation inside the system, and changes in system orientation.

Figure 6A:
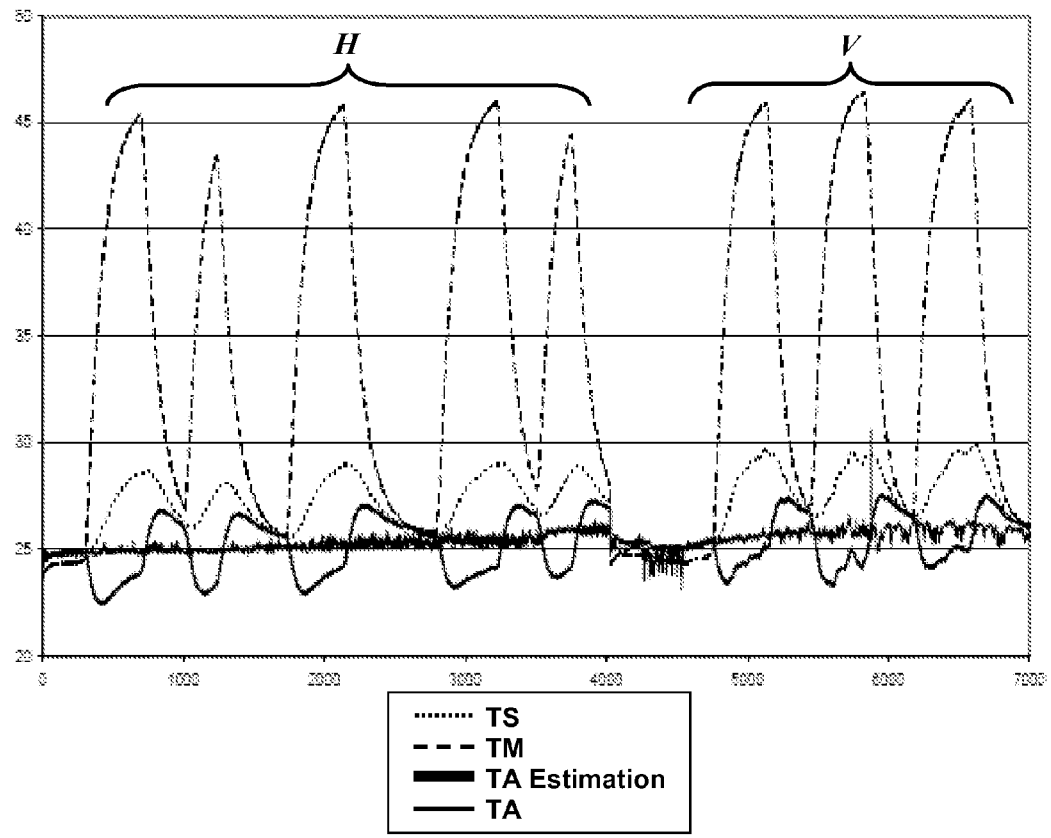
FIGS. 6A and 6B show the results of an evaluation of another embodiment of the present invention that was designed to increase the effective surface contact area between the second temperature sensor and the ambient environment, and the temperature error associated with the test, respectively.

The measurements depicted in the FIGS. 5A and 5B were made while the system was oriented horizontally, i.e., while at rest on a flat surface with the long axis of the device oriented substantially parallel to the surface. When the system was moved to a vertical orientation (i.e., with the long axis of the device oriented substantially perpendicular to the surface—if the device did not have a long axis, "vertical" orientation would refer to the condition whereby the axis formed by an imaginary line between the second temperature sensor and a heat source is substantially perpendicular to the surface), the simplified thermal model showed additional errors due to heat convection towards the cavity that enclosed the second temperature sensor (results not shown). To reduce the effect of heat convection when the system is oriented vertically, a heat convection barrier was incorporated into the system (see, e.g., item 13 in FIG. 2), separating the interior space into two portions, one of which contained the heat source, and the other of which contained the cavity enclosing the sensor/plate arrangement. The first temperature sensor was located in the same space within the housing (i.e., on the same side of the heat convection barrier) in which the cavity enclosing the sensor/plate arrangement was located. The first temperature sensor was located inside a microprocessor mounted on a printed circuit board (PCB), which was disposed such that a portion of the board was on one side of the heat convection barrier, and the remaining portion of the board was on the opposite side of the heat convection barrier. The heat source (a resistor) was mounted on the portion of the PCB that was on the opposite side of the heat convection barrier from the first temperature sensor. Instead of a single PCB, an alternative arrangement may include two separate PCBs linked by a board-to-board connector, wherein the respective PCBs are on opposite sides of the heat convection barrier. The system with the heat convection barrier was tested in both the horizontal and vertical orientation, and it was found that the barrier effectively eliminated the effect of system orientation on the temperature calculation. Results are shown in FIG. 6A, wherein the peaks labeled "H" correspond to temperature readings obtained while the system was in the horizontal orientation, peaks labeled "V" correspond to temperature readings obtained while the system was in the vertical orientation, TS represents the temperature readings acquired by the second temperature sensor, TM represents the temperature readings acquired by the first temperature sensor, TA Estimation represents the ambient temperature as calculated by the system using the first and second temperature sensor readings, and TA is the actual ambient temperature as separately measured within the test chamber.

Figure 6B:
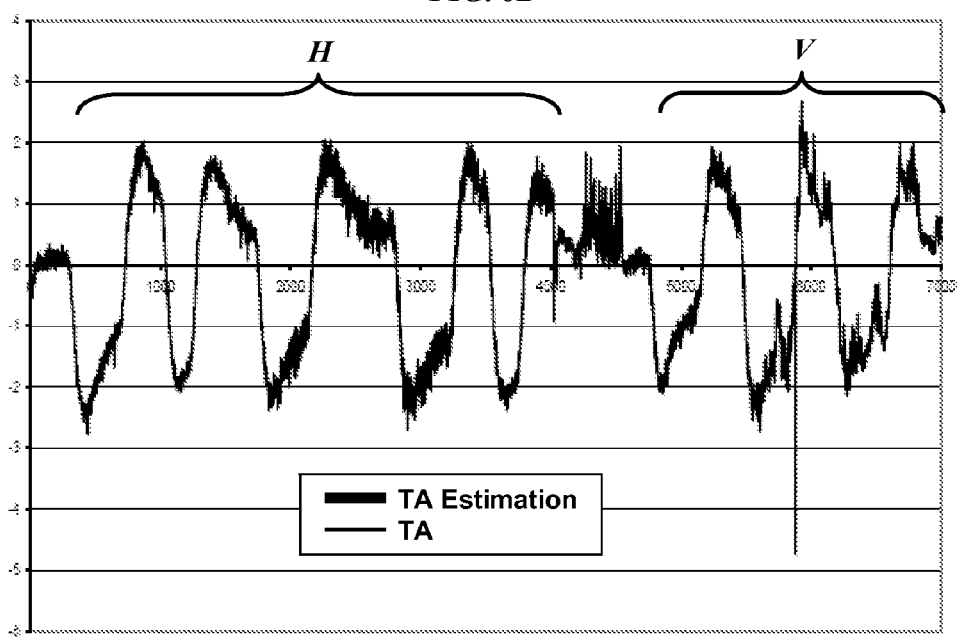

FIG. 6B shows the temperature error in the calculation of the temperature of the ambient environment outside of the housing (which is equivalent to a temperature associated with an analyte measurement component, a test strip, or both), wherein the peaks labeled "H" correspond to error in the temperature readings obtained while the system was in the horizontal orientation, and peaks labeled "V" correspond to error in the temperature readings obtained while the system was in the vertical orientation. Results are shown in 5 second intervals.

The preceding experiments demonstrate that, inter alia, the measurement of temperature associated with an analyte measurement process is improved using the present dual sensor approach, and that accurate temperature measurement can occur regardless of device orientation and fluctuations in power dissipation. The present approach also reduces the amount of time a user must wait to use the biosensing instrument measurement after the instrument has been moved between locations that are respectively characterized by different ambient temperature conditions. Such advantages improve the ability of the biosensing instrument to provide accurate readings regarding analyte levels. In addition, the systems described herein are suitable for use in connection with modern handheld devices that feature a compact design.

The disclosures of each patent, patent application, and publication cited or described in this document are hereby incorporated herein by reference, in their entirety.

As employed above and throughout the disclosure, the following terms and abbreviations, unless otherwise indicated, shall be understood to have the following meanings. In the present disclosure the singular forms "a," "an," and "the" include the plural reference, and reference to a particular numerical value includes at least that particular value, unless the context clearly indicates otherwise. Thus, for example, a reference to "a heat source" is a reference to one or more of such heat sources and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive; as another example, the phrase "about 8%" preferably refers to a value of 7.2% to 8.8%, inclusive. Where present, all ranges are inclusive, divisible, and combinable. For example, when a range of "1 to 5" is recited, the recited range should be construed as including ranges "1 to 4", "1 to 3", "1-2", "1-2 and 4-5", "1-3 and 5", and the like.

What is claimed:

1. A method for calculating temperature associated with a test strip inserted in an analyte assessing system comprising:
    measuring a first temperature at a first position that is in thermal communication with a heat source in said analyte assessing system;
    measuring a second temperature at a second position in said analyte assessing system that is in thermal communication with said heat source to a lesser extent relative to said first position; and,
    using the measured first temperature and the measured second temperature to calculate the temperature associated with said test strip,
    wherein
    said first temperature is measured by a first temperature sensor and said second temperature is measured by a second temperature sensor;
    said system comprises a housing that encloses said first temperature sensor and said second temperature sensor, a first opening in said housing at a location proximal to said second temperature sensor, a second opening at a second location in said housing, and a channel extending between said first opening and said second opening and containing said second temperature sensor, wherein each of said openings place said channel in fluid communication with the ambient environment outside of said housing, and,
    ambient air contacts said second temperature sensor and displaces heated air proximate said second temperature sensor.

2. The method according to claim 1 wherein insulating material is interposed between said second temperature sensor and said heat source.

3. The method according to claim 1 wherein insulating material is interposed between said second temperature sensor and said first temperature sensor.

4. The method according to claim 1 further comprising compensating for said calculated temperature associated with said test strip during a measurement of an analyte on said test strip.

5. The method according to claim 1 wherein said temperature associated with said test strip is calculated by a processor housed within said system.

6. The method according to claim 5 wherein said processor is in electronic communication with a first temperature sensor that measures said first temperature, and with a second temperature sensor that measures said second temperature.

7. The method according to claim 5 wherein said processor calculates said temperature (TA) associated with said test strip by performing a calculation according to formula (I)

$$TA = TS + \frac{K}{K-1}(TM - TS) \quad (I)$$

wherein TS is the temperature measured by said second temperature sensor, TM is the temperature measured by the first temperature sensor, and K is defined by $$K = \frac{(TS - TA)}{(TM - TA)}$$

wherein TS is the temperature measured by the second temperature sensor, TA is the actual temperature of the ambient environment outside of said housing, and TM is the temperature measured by the first temperature sensor.

8. The method according to claim 1 wherein said housing substantially defines an internal space, and wherein said second temperature sensor is positioned proximate an opening in said housing.

9. The method according to claim 8 wherein said system is configured to reduce the heat transfer resistance between the second temperature sensor and the ambient environment outside of said housing.

10. The method according to claim 8 wherein said system further comprises insulating material that at least partially isolates said second temperature sensor, said heat conductive material, and said opening from the remainder of the internal space of said housing.

11. The method according to claim 8 wherein heat conductive material is disposed between said second temperature sensor and said opening in said housing.

12. The method according to claim 11 wherein said second temperature sensor is mounted on said heat conductive material.

13. The method according to claim 11 wherein said heat conductive material comprises metal or plastic.

14. A method for calculating temperature associated with a test strip inserted in an analyte assessing system comprising:
measuring a first temperature at a first position that is in thermal communication with a heat source in said analyte assessing system;
measuring a second temperature at a second position in said analyte assessing system that is in thermal communication with said heat source to a lesser extent relative to said first position; and,
using the measured first temperature and the measured second temperature to calculate the temperature associated with said test strip,
wherein
said temperature associated with said test strip is calculated by a processor housed within said system, and,
said processor calculates said temperature (TA) associated with said test strip by performing a calculation according to formula (I)

$$TA = TS + \frac{K}{K-1}(TM - TS) \quad (I)$$

wherein TS is the second temperature, TM is the first temperature, and K is defined by $$K = \frac{(TS - TA)}{(TM - TA)}$$

wherein TS is the second temperature, TA is the actual temperature of the ambient environment outside of said housing, and TM is the first temperature.

15. The method according to claim 14 wherein said processor is in electronic communication with a first temperature sensor that measures said first temperature, and with a second temperature sensor that measures said second temperature.

16. The method according to claim 14 wherein said first temperature is measured by a first temperature sensor and said second temperature is measured by a second temperature sensor, and wherein said first temperature sensor and said second temperature sensor are each housed within said system.

17. The method according to claim 16 wherein insulating material is interposed between said first temperature sensor and said heat source.

18. The method according to claim 16 wherein insulating material is interposed between said second temperature sensor and said heat source.

19. The method according to claim 16 wherein insulating material is interposed between said second temperature sensor and said first temperature sensor.

20. The method according to claim 16 wherein said system comprises a housing that encloses said first temperature sensor and said second temperature sensor and substantially defines an internal space, and wherein said second temperature sensor is positioned proximate an opening in said housing.

21. The method according to claim 20 wherein said system is configured to reduce the heat transfer resistance between the second temperature sensor and the ambient environment outside of said housing.

22. The method according to claim 20 wherein said system further comprises insulating material that at least partially isolates said second temperature sensor, said heat conductive material, and said opening from the remainder of the internal space of said housing.

23. The method according to claim 20 wherein heat conductive material is disposed between said second temperature sensor and said opening in said housing.

24. The method according to claim 23 wherein said second temperature sensor is mounted on said heat conductive material.

25. The method according to claim 23 wherein said heat conductive material comprises metal or plastic.

* * * * *